United States Patent
Aida

(10) Patent No.: US 6,777,178 B1
(45) Date of Patent: Aug. 17, 2004

(54) ANTIBODIES FOR JUDGING POSSIBILITY OF THE ONSET OF BOVINE LEUKEMIA

(75) Inventor: Yoko Aida, Ibaraki (JP)

(73) Assignee: Riken, Saitama (JP)

(*) Notice: Subject to any disclaimer, the term of this patent is extended or adjusted under 35 U.S.C. 154(b) by 0 days.

(21) Appl. No.: 09/763,625

(22) PCT Filed: Sep. 7, 1999

(86) PCT No.: PCT/JP99/04834

§ 371 (c)(1),
(2), (4) Date: Jun. 4, 2001

(87) PCT Pub. No.: WO00/14214

PCT Pub. Date: Mar. 16, 2000

(30) Foreign Application Priority Data

Sep. 7, 1998 (JP) .......................................... 10/252128

(51) Int. Cl.[7] ............................ C12Q 1/70; C12Q 1/68; C07K 16/00
(52) U.S. Cl. .......................... 435/5; 435/6; 530/388.73; 530/388.8
(58) Field of Search ............................. 435/5, 6, 91.2; 530/388.73, 388.8

(56) References Cited

U.S. PATENT DOCUMENTS

| | | | |
|---|---|---|---|
| 5,567,809 A | 10/1996 | Appple et al. | |
| 5,582,987 A | 12/1996 | Lewin et al. | |
| 6,090,540 A | 7/2000 | Aida | |

FOREIGN PATENT DOCUMENTS

WO            98/03680            1/1998

OTHER PUBLICATIONS

Aida et al., "Tumor–associated MΓ 34,000 and MΓ 32,000 Membrane Glycoproteins that are Serine Phosphorylated Specifically in Bovine Leukemia Virus–induced Lymphosarcoma Cells", *Cancer Research*, 52:6463–6470 (1992).

Aida et al., "Phenotype and Ontogeny of Cells Carrying a Tumor–associated Antigen that is Expressed on Bovine Leukemia Virus–induced Lymphosarcoma", *Cancer Research*, 53, pp. 429–437 (1993).

Aida et al., "Identification of a New Bovine MHC Class II DRB Allele by Nucleotide Sequencing and an Analysis of Phylogenetic Relationships", *Biochemical and Biophysical Research Communications*, vol. 209, No. 3, pp. 981–988 (1995).

Aida et al., "Tumor–associated Antigens on Bovine Leukemia Virus–induced Bovine Lymphosarcoma Identified by Monoclonal Antibodies", *Cancer Research*, 45, pp. 1174–1180 (1985).

Miyasaka et al., "Sheep as an Experimental Model for Immunology: Immunological Techniques in Vitro and in Vivo", *Immunological Methods*, vol. III, pp. 403–423 (1985).

Aida et al., "Cloning of cDNAs and Molecular Evolution of a Bovine MHC Class II DRA Gene", *Biochem. Biophys. Res. Commun.*, 204, pp. 195–202 (1994).

Armstrong et al., "Preferential Site–dependent Cleavage by Restriction Endonuclease PstI", *Nucleic Acids Research*, vol. 10, No. 3, pp. 993–1007 (1982).

Brooker, *Genetics Analysis and Principles*, p. 79 (1999).

Hughes et al., "Proviruses of Avian Sarcoma Virus are Terminally Redundant, Co–extensive with Unintegrated Linear DNA and Integrated at Many Sites", *Cell*, vol. 15, pp. 1397–1410 (1978).

Levy et al., "Bovine Leukemia Virus Specific Antibodies Among French Cattle. I. Comparison of Complement Fixation and Hematological Tests", *Int. J. Cancer*, 19, 882–827 (1977).

McKnight, "The Induction of Ovalbumin and Conalbumin mRNA by Estrogen and Progesterone in Chick Oviduct Explant Cultures", *Cell*, vol. 14, pp. 403–413 (1978).

Stone et al., "Up–regulation of IL–2 Receptor $\alpha$ and MHC Class II Expression on Lymphocyte Subpopulations from Bovine Leukemia Virus Infected Lymphocytotic Cows", *Veterinary Immunology and Immunopathology*, 48, pp. 65–76 (1995).

Stone et al., "Modulation of Bovine Leukemia Virus–associated Spontaneous Lymphocyte Proliferation by Monoclonal Antibodies to Lymphocyte Surface Molecules", *Clinical Immunology and Immunovirology*, vol. 83, No. 2, pp. 156–164 (1997).

"Enzootic Bovine Leukosis", Alberta Agriculture Food and Rural Development, www.agric.gov.ab.ca/agdex/600/63–07.html, pp. 1–4 (1996).

Aida et al., "Identification of Tumor–Associated Antigen that is Expressed on Bovine Leukemia Virus–Induced Lymphosarcoma Cells and Expression of its Human Homologue in Human T–cell Lymphotrophic Virus I–infected Cell Lines", *Leukemia*, vol. 8, pp. 231–234 (1994).

Koguchi et al. "Changes in the Distribution of Cells Expressing Tumor–Associated Antigen in Lymph Nodes during the Progression of Enzootic Bovine Leukosis" *J. Compara. Pathol*, vol. 115, pp. 343–352 (1996).

Primary Examiner—Hankyel T. Park
(74) Attorney, Agent, or Firm—Greenblum & Bernstein, P.L.C.

(57) ABSTRACT

A c143 monoclonal antibody which is used for detecting a bovine individual having a possibility of onset of bovine leukemia; a monoclonal antibody which is used for detecting a bovine individual having a possibility of onset of bovine leukemia, wherein the monoclonal antibody has the substantially same reactivity as the c143 monoclonal antibody to a bovine MHC Class II DR molecule to which a possibility of onset of bovine leukemia is attributable; and an agent for diagnosing a possibility of onset of bovine leukemia which comprises the aforementioned monoclonal antibody. Bovine individuals having a possibility of onset of bovine leukemia can be conveniently and accurately detected.

6 Claims, No Drawings

ANTIBODIES FOR JUDGING POSSIBILITY OF THE ONSET OF BOVINE LEUKEMIA

TECHNICAL FIELD

The present invention relates to a monoclonal antibody which is used for judging a possibility of the onset of bovine leukemia caused by bovine leukemia virus BLV.

Background Art

The major histocompatibility antigens (MHC antigens) are molecules involved in self-nonself differentiation in the defense mechanism of the living body against infection. They are classified into Class I molecule composed of α chain and β2M, and class II molecule composed of α chain and β chain. A groove for trapping an antigen peptide is present on the α1 and α2 domains, and also on the α1 and β1 domains. They are featured to have the T cell receptor recognize only a fragmented peptide trapped in the groove, thereby achieve cell death (cellular immunity) by CD8+ cells which have recognized the class I antigens, as well as induce mainly antibody production (humoral immunity) by CD4+ cells which have recognized the class II antigens.

The MHC genes constitute a gene group most full of polymorphism, and the locations of pockets, shapes, sizes, and properties of the peptide trapping grooves are different among haplotypes. It is considered that association conditions of the trapped fragment peptides may vary depending on these differences, which decide immune response and disease sensitivity of each individual. The correlation between the MHC haplotypes and a resistance to a disease (disease insusceptibility) or a possibility of the onset of a disease (disease susceptibility) has been reported, for example, as to human immune deficiency virus (HIV), human T cell leukemia virus (HTLV) and malaria.

As for the bovine MHC (BoLA) class II genes, the existence of DQA, DQB, DRA, DRB, DNA, DOB, DYA, and DYB genes has been estimated so far. DRB3, inter alia, which is one of the three genes (DRB1 to B3) identified on the DRB genetic locus, has been known to encode a functional protein, and the existence of 73 alleles has been revealed so far. However, there is almost no report about correlation between bovine infectious diseases and the bovine MHC (BoLA) haplotypes.

In particular, as to the bovine leukemia virus (BLV), which has the gene pX that regulates virus proliferation in the same manner as the human immunodeficiency virus (HIV) and is a retrovirus most related to HTLV-I, a research group in the United States has reported its relationship with the bovine MHC (BoLA) haplotypes mainly focusing disease resistance; however, its relationship with possibility of onset of the leukemia has not been reported. The ratio of cattle infected by this virus (infection rate in Japan) is 10 to 20%, and 1 to 2% of the infected cattle develops extremely malignant endemic bovine leukemia to die after a long latent period of 10 to 15 years. Therefore, economic loss of stockbreeders caused by the virus is very serious. If a possibility of the onset of cattle after BLV infection can be evaluated by the analysis of bovine MHC (BoLA) haplotypes, it becomes possible to preliminarily select disease resistant cattle for breeding beforehand, and it is expected that extremely safe cattle breeding can be continued.

The inventors of the present invention previously analyzed the structure of DRB gene locus among the bovine MHC (BoLA) class II genes, and reported the structures of DRB3 gene (BoLA-DRB3) and the gene product thereof (Biochem. Biophys. Res. Commun., 209, pp.981–988, 1995). The inventors further studied the function of the gene and found that a portion is present, whose amino acid sequence is distinctly different between cattle developing the leukemia and cattle not developing the disease, in the gene product from the second exon (β1 domain) of BoLA-DRB3 showing particularly noticeable polymorphism. They also found that the amino acid substitutions directly correlated with disease susceptibility to BLV and disease resistance. Moreover, they found that, in judging a possibility of the onset of bovine leukemia caused by bovine leukemia virus BLV, a bovine individual, in which an amino acid sequence defined by the amino acid numbers 75 to 78 of the β1 domain of the bovine MHC Class II DR β chain is Val-Asp-Thr-Tyr, can be judged to have a possibility of the onset of the leukemia, and they achieved the invention relating to the method (International Publication WO98/3680).

A monoclonal antibody (c143 monoclonal antibody) is known to react with a tumor-associated antigen that is excessively expressed in BLV infected cells with progress of pathologic state of bovine leukemia ((a) Aida, Y. et al., Cancer Research, 52, pp.6463–6470, 1992; (b) Aida, Y. et al., Cancer Research, 53, pp.429–437, 1993). The aforementioned publications (a) (p.6469, the left column) and (b) (p.436, the left column) suggested that the tumor-associated antigen recognized by the aforementioned monoclonal antibody is related to an MHC Class II antigen. However, details of the reaction between the monoclonal antibody and the MHC Class II antigens have not been elucidated, and moreover, the structure of the epitope of the aforementioned monoclonal antibody has not been known so far.

DISCLOSURE OF THE INVENTION

When the aforementioned method of judgment (WO98/3680) is carried out, it is necessary to collect a sample of a living bovine individual, amplify a desired gene, and then determine a base sequence of exon 2 gene of BoLA-DRB3, or carry out the PCR-RFLP method. The aforementioned publication discloses a primer set useful for the judging method; however, it is troublesome and time-consuming to carry out the aforementioned judging method for numbers of bovine individuals. Accordingly, it has been desired to develop a more simple method for judgment.

Therefore, an object of the present invention is to provide a means of simply and accurately judging a possibility of onset of leukemia in bovine individuals caused by bovine leukemia virus (BLV). More specifically, the object is to provide a means of accurately judging a possibility of onset of leukemia in bovine individuals caused by bovine leukemia virus without necessity of determination of a base sequence of exon 2 of the BoLA-DRB3.

The inventors of the present invention made intensive studies to achieve the foregoing objects. As a result, they found that bovine individuals having a gene, encoding β1 domain of the MHC Class II DR β chain and attributable to a possibility of the onset of bovine leukemia, can be detected with a monoclonal antibody which reacts with a tumor-associated antigen excessively expressed in BLV infecting cells (the c143 monoclonal antibody), and that a possibility of the onset of leukemia can be judged with extremely high accuracy. The present invention was achieved on the basis of the aforementioned findings.

The present invention thus provides c143 monoclonal antibody which is used, for detecting a bovine individual which has a possibility of onset of bovine leukemia; c143 monoclonal antibody which is used for detecting a gene encoding β1 domain of the bovine MHC Class II DR β chain to which a possibility of onset of bovine leukemia is attributable; and c143 monoclonal antibody which is used for detecting a bovine individual which has a gene encoding β1 domain of the MHC Class II DR β chain to which a possibility of onset of bovine leukemia is attributable.

In addition, there are provided a monoclonal antibody which is used for detecting a gene encoding β1 domain of the bovine MHC Class II DR β chain to which a possibility of the onset of bovine leukemia is attributable, wherein the monoclonal antibody has substantially the same reactivity as c143 monoclonal antibody to bovine MHC Class II DR molecule to which a possibility of onset of bovine leukemia is attributable; a monoclonal antibody which is used for detecting a bovine individual having a gene encoding β1 domain of the MHC Class II DR β chain to which a possibility of the onset of bovine leukemia is attributable, wherein the monoclonal antibody has substantially the same reactivity as c143 monoclonal antibody to bovine MHC Class II DR molecule to which a possibility of the onset of bovine leukemia is attributable; and a monoclonal antibody which is used for detecting a bovine individual which has a possibility of onset of bovine leukemia, wherein the monoclonal antibody has substantially the same reactivity as c143 monoclonal antibody to bovine MHC Class II DR molecule to which a possibility of onset of bovine leukemia is attributable.

According to another aspect of the present invention, there is provided an agent for diagnosing a possibility of the onset of bovine leukemia which comprises the aforementioned monoclonal antibody, preferably the aforementioned c143 monoclonal antibody. There are also provided a method for detecting a gene encoding β1 domain of bovine MHC Class II DR β chain to which a possibility of onset of bovine leukemia is attributable by means of c143 monoclonal antibody; a method for detecting a bovine individual having a gene encoding β1 domain of MHC Class II DR β chain to which a possibility of onset of bovine leukemia is attributable by means of c143 monoclonal antibody; and a method for detecting a bovine individual which has a possibility of onset of bovine leukemia by means of c143 monoclonal antibody.

According to still another aspect, there are provided a monoclonal antibody which is capable of detecting a gene encoding β1 domain of bovine MHC Class II DR β chain to which a possibility of onset of bovine leukemia is attributable; a monoclonal antibody which is capable of detecting a bovine individual having a gene encoding β1 domain of MHC Class II DR β chain to which a possibility of the onset of bovine leukemia is attributable; and a monoclonal antibody which capable of detecting a bovine individual having a possibility of onset of bovine leukemia. A preferred example of the monoclonal antibody is c143 monoclonal antibody.

BEST MODE FOR CARRYING OUT THE INVENTION

Cattle to be applied with the method of the present invention are not particularly limited. The method may be applied to any sorts of cattle including dairy cattle, dairy and beef cattle, beef cattle, working cattle, working and beef cattle and the like, so long as they have a possibility of infection by leukemia virus BLV and have a possibility of developing the leukemia owing to the infection. More specifically, examples include Japanese cattle such as Japanese Black and Japanese Shorthorn, or breeds such as Holstein, Jersey, Hereford, Aberdeen Angus, and Friesian. However, breeds are not limited to these examples.

As the monoclonal antibody of the present invention, c143 monoclonal antibody can preferably be used. In addition to the c143 monoclonal antibody, monoclonal antibodies may also be used which have substantially the same reactivity as the c143 monoclonal antibody to bovine MHC Class II DR molecule to which a possibility of onset of bovine leukemia is attributable. The wording "MHC Class II DR molecule" used in the present specification means a molecule that contains a part or all of the MHC Class II DR α chain and a part or all of the MHC Class II DR β chain.

The monoclonal antibody having substantially the same reactivity as the c143 monoclonal antibody can easily be chosen by persons skilled in the art on the basis of criteria whether or not the monoclonal antibody gives a result of judgment similar to that obtained by the c143 monoclonal antibody when diagnosis is carried out in accordance with the method specifically described in Examples of the present specification. As such monoclonal antibodies, those derived from appropriate mammals including mice, rats and rabbit can be used. The c143 monoclonal antibody (mouse, IgG2b) can easily be prepared by persons skilled in the art by a method described in literature (Aida, Y. et al., Cancer Res., 45, pp.1174–1180, 1985).

As for an amino acid sequence specified by the amino acid numbers of 75 to 78 of the β1 domain of the bovine MHC Class II DR β chain of a bovine individual, when the amino acid sequence (the amino acid numbers 75 to 78) is Val-Asp-Thr-Tyr in both of the alleles, it is known that the bovine individual has a high risk of onset of the leukemia when the individual has been already infected by the bovine leukemia virus BLV, or when the individual becomes infected by the virus (International Publication WO98/3680: The disclosures of the publication are incorporated herein as disclosures of the present specification.). Whilst when the amino acid sequences in the alleles are heterozygote of Val-Asp-Thr-Tyr (VDTY) and Val-Asp-Thr-Val (VDTV); heterozygote of Val-Asp-Thr-Tyr (VDTY) and Val-Asp-Arg-Val (VDRV); homozygote of Val-Asp-Thr-Val (VDTV); homozygote of Val-Asp-Arg-Val (VDRV); heterozygote of Val-Asp-Arg-Val (VDRV) and Val-Asp-Thr-Val (VDTV) or the like, the bovine individual has a very low possibility of onset of the leukemia even if the bovine individual has been already infected by the bovine leukemia virus BLV or when the individual becomes infected by the virus.

Although it is not intended to be bound by any specific theory, the monoclonal antibody of the present invention, preferably the c143 monoclonal antibody, binds to the bovine MHC Class II DR molecule, and has high reactivity when the molecule has Val-Asp-Thr-Tyr (the amino acid numbers 75 to 78) in the amino acid sequence of its β chain. Accordingly, a bovine individual wherein high reactivity of the monoclonal antibody of the present invention is observed has a gene that codes for Val-Asp-Thr-Tyr (the amino acid numbers 75 to 78) in β1 domain of MHC Class II DR β chain (a gene to which a possibility of the onset of bovine leukemia is attributable), and said individual has a high possibility of onset of bovine leukemia. The amino acid sequence of the β1 domain of the bovine MHC Class II DR β chain has been reported by Aida et al. (Aida, Y., et al., Biochem. Biophys. Res. Commun., 209, pp.981–988, 1996).

The method for detecting a gene that encodes the β1 domain of the bovine MHC Class II DR β chain, to which a possibility of onset of bovine leukemia is attributable, is not particularly limited, and any methods may be applied so long as they can detect a binding between the monoclonal antibody and the antigen. For example, any detecting method available to persons skilled in the art can be applied, including fluorescent antibody method, flow cytometry, ELISA, immunohistological assay and the like. In order to facilitate the detection; a monoclonal antibody labeled with a fluorescent substance, radioisotope, avidin (or biotin) or the like can be used as the monoclonal antibody. Such labeling methods are well-known to persons skilled in the art, and any appropriate means can be applied.

In a preferred embodiment of the present invention, reactivity between the bovine MHC Class II DR molecule and the monoclonal antibody can be examined by using lymphocytes as samples which are separated or collected from a bovine individual. For example, peripheral lymphocytes can be also prepared from leukocytes by collecting peripheral blood from a bovine individual by using a syringe containing an anticoagulant, obtaining a leukocyte layer by centrifugation under the conditions of 4° C. and 3,000 rpm for 20 minutes, and then treating the layer by the method of Miyasaka et al. (Miyasaka, M. and Trnka, Z., Immunological Methods, Vol.3, pp.403–423, 1985, Academic Press, NY.).

When the monoclonal antibody of the present invention has high reactivity to the peripheral lymphocyte, the bovine individual is judged to have a possibility of onset of bovine leukemia. As the sample, a section of the lymph node, tumor tissues or the like may also be used. The degree of reactivity of the monoclonal antibody can be examined usually by preparing a control group or using a standard sample and the like. In addition, a gene encoding bovine MHC Class II DR molecule is amplified by the PCR method, and then reactivity of the monoclonal antibody to the gene product may be investigated.

The diagnostic agent of the present invention comprises the aforementioned monoclonal antibody as an active ingredient, and is used for judgment whether or not a bovine individual has a possibility of onset of bovine leukemia. In general, it is known that diagnostic agents comprising a monoclonal antibody can be formulated in various forms, and accordingly, the diagnostic agent of the present invention can be formulated in any appropriate forms. For example, the agent can be provided as preparations in a freeze-dried form or those in a liquid form or the like. The diagnostic agent of the present invention can be prepared by using one or more kinds of appropriate additives for formulation depending on a form thereof. As the additives for formulation, for example, pH adjusting agents, dissolving aids, antiseptics, buffering agents, excipients and the like can be used. However, the additives are not limited to these examples.

EXAMPLES

The present invention will be explained more specifically by referring to examples. However, the scope of the present invention is not limited to the examples set out below.

1. Materials and Methods

Peripheral blood lymphocytes were fractioned from bovine individuals having a gene that codes for bovine MHC Class II DR β chain, to which resistance or sensitivity to onset of leukemia caused by BLV being attributable, and then mRNAs were extracted. cDNAs were synthesized with a reverse transcriptase by using an oligo (DT) primer and the mRNAs as templates. Then, using the resulting cDNAs as templates, cDNA clones containing the entire encoding region of DR β chain were isolated by the PCR method using the two primers:
5'-TGGCTCGAGCCTCTGCTGTTCTCCGGCAT-3' and
5'-TGGTCTAGAACTTCAGCTCAGGAGCCCTG-3'.
The primers used were designed to have XhoI and XbaI sites. The resulting PCR products (cDNA clones) were subcloned to a sequencing vector, and then the base sequences were determined to verify that desired genes were obtained.

As alleles of the gene encoding β1 domain of MHC Class II DR β chain (hereinafter referred to as "BoLA-DRB3") to which resistance to leukemia caused by BLV is attributable, cDNAs of *0902, *0701, *1101, and *1401 were isolated. As the BoLA-DRB3 alleles responsible for sensitivity to the leukemia, cDNAs of *1501, *1601, *1302, and *1001 were isolated. Each cDNA was inserted into expression vector pME18Neo at XhoI and XbaI sites, and temporally co-transformed into COS1 cells or the 23CLN cells together with an expression vector previously isolated which was inserted with a cDNA clone containing the entire coding region of α chain (Aida, A., et al., Biochem. Biophys. Res. Commun., 204, pp.195–202, 1994). About 40 hours after the transformation, indirect immunofluorescence and flowcytometry were carried out using c143 monoclonal antibody to analyze reactivity.

2. Results

The c143 monoclonal antibody strongly reacted with the DR antigen-expressing cells introduced with the cDNA of BoLA-DRB3 gene responsible for sensitivity to onset of leukemia caused by BLV. Among them, the c143 monoclonal antibody had extremely strong reactivity to cells under expression which was introduced with *1601 cDNA, an allele most frequently found in cattle after the onset of leukemia. The results are shown in Table 1 set out below. In the table, * reactivity was classified into +: weak, ++: medium, and +++: strong on the basis of reactivity to c143 monoclonal antibody; an allele encoding V as an amino acid. residue of amino acid number 78 in DR β chain was judged as resistant to the onset of leukemia, whilst an allele encoding Y as disease susceptible; * BoLA-DRB3 *1601 cDNA clone has already been isolated and referred to as NR1 (Aida, Y. et al., Biochem. Biophys. Res. Commun., 209, pp.981–988, 1995).

TABLE 1

| cDNA of α chain/cDNA of β chain | Amino acid residue of amino acid number 78 of DR β chain: V or Y** | Reactivity to c143 antibody* |
|---|---|---|
| MR1/BoLA-DRB3*0902 | V | + |
| MR1/BoLA-DRB3*0701 | V | + |
| MR1/BoLA-DRB3*1101 | V | + |
| MR1/BoLA-DRB3*1401 | V | + |
| MR1/BoLA-DRB3*1501 | Y | ++ |
| MR1/BoLA-DRB3*1601 (NR1)*** | Y | +++ |
| MR1/BoLA-DRB3*1302 | Y | ++ |
| MR1/BoLA-DRB3*1001 | Y | ++ |

Industrial Applicability

By using the monoclonal antibody of the present invention, a possibility of onset of bovine leukemia virus (BLV) of bovine individuals can be conveniently and accurately judged.

What is claimed is:

1. A method for detecting a bovine individual which has a possibility of onset of bovine leukemia comprising binding a c143 monoclonal antibody with a tumor associated antigen.

2. A method for detecting a bovine individual which has a possibility of onset of bovine leukemia comprising detecting a gene encoding β1 domain of bovine MHC Class II DR β chain to which a possibility of onset of bovine leukemia is attributable with a c 143 monoclonal antibody.

3. A method for detecting a bovine individual which has a possibility of onset of bovine leukemia comprising binding a monoclonal antibody with a tumor associated antigen, the monoclonal antibody having substantially a same reactivity as a c143 monoclonal antibody to a bovine MHC Class II DR molecule to which a possibility of onset of bovine leukemia is attributable.

4. A method for detecting a bovine individual which has a possibility of onset of bovine leukemia comprising detecting a gene encoding β1 domain of bovine MHC Class II DR β chain to which a possibility of onset of bovine leukemia is attributable with a monoclonal antibody, the monoclonal antibody having substantially a same reactivity as a c143 monoclonal antibody to a bovine MHC Class II DR molecule to which a possibility of onset of bovine leukemia is attributable.

5. A diagnostic composition for detecting a bovine individual which has a possibility of onset of bovine leukemia comprising c143 monoclonal antibody as an active ingredient.

6. A diagnostic composition for detecting a bovine individual which has a possibility of onset of bovine leukemia comprising a monoclonal antibody as an active ingredient, said monoclonal antibody having substantially a same reactivity as a c143 monoclonal antibody to a bovine MHC Class II DR molecule to which a possibility of onset of bovine leukemia is attributable.

* * * * *